United States Patent
Yamagata

(10) Patent No.: US 8,703,054 B2
(45) Date of Patent: Apr. 22, 2014

(54) DIRECTION SELECTION MECHANISM FOR ANALYTICAL TOOL, AND ANALYTICAL DEVICE

(75) Inventor: Hidenari Yamagata, Kyoto (JP)

(73) Assignee: ARKRAY, Inc., Kyoto-shi (JP)

( * ) Notice: Subject to any disclaimer, the term of this patent is extended or adjusted under 35 U.S.C. 154(b) by 1828 days.

(21) Appl. No.: 11/628,176

(22) PCT Filed: Jun. 1, 2005

(86) PCT No.: PCT/JP2005/010079
§ 371 (c)(1),
(2), (4) Date: Nov. 30, 2006

(87) PCT Pub. No.: WO2005/119268
PCT Pub. Date: Dec. 15, 2005

(65) Prior Publication Data
US 2007/0231212 A1    Oct. 4, 2007

(30) Foreign Application Priority Data
Jun. 2, 2004    (JP) ................................ 2004-164983

(51) Int. Cl.
    *G01N 21/13*    (2006.01)
(52) U.S. Cl.
    USPC ................................ 422/63; 436/46; 436/48
(58) Field of Classification Search
    USPC .......... 436/44, 46, 47, 48; 221/156, 162, 171, 221/172, 194, 224, 259; 422/55, 63, 68.1, 422/82.05, 99, 102, 104, 500, 511, 64–67; 414/222.01, 222.02, 222.04, 222.08, 414/226.04, 226.05, 331.01, 331.13, 425, 414/589, 749.1, 749.5, 754, 757, 780, 781, 414/806
    See application file for complete search history.

(56) References Cited

U.S. PATENT DOCUMENTS

| 4,777,907 | A | * | 10/1988 | Sanger | 118/687 |
| 4,972,935 | A |   | 11/1990 | Gross et al. | |
| 5,097,938 | A |   | 3/1992 | Grüner et al. | |
| 5,556,597 | A |   | 9/1996 | Shindo et al. | |
| 6,685,052 | B1 | * | 2/2004 | Nemoto et al. | 221/157 |
| 7,381,375 | B2 | * | 6/2008 | Ravkin et al. | 422/552 |
| 2001/0020567 | A1 | * | 9/2001 | Saito et al. | 198/396 |
| 2002/0006362 | A1 | * | 1/2002 | Ohta et al. | 422/102 |
| 2004/0104241 | A1 | * | 6/2004 | Broussard et al. | 221/289 |

FOREIGN PATENT DOCUMENTS

| JP | 6-99018 | 12/1994 |
| JP | 7-306206 | 11/1995 |
| JP | 2000-35433 | 2/2000 |

OTHER PUBLICATIONS

International Search Report for corresponding International application PCT/JP2005/010079, mailed Sep. 13, 2005.

* cited by examiner

*Primary Examiner* — Jan Ludlow
(74) *Attorney, Agent, or Firm* — Fox Rothschild LLP

(57) ABSTRACT

The present invention relates to analytical apparatus comprising: a passage (45) in which an analytical tool (2) is moved from above to below; and a movement block (51), made capable of reciprocatory movement in the horizontal directions (D1, D2), for moving the analytical tool (2) incoming through the passage (45) in the direction (D1). This analytical apparatus is constructed such that, by erecting the analytical tool (2) on the movement block (51) positioned directly below the outlet (45B) of the passage (45) and causing the movement block (51) to move in the D1 or D2 direction, the analytical tool (2) is tipped over, and the analytical tool (2) is placed in a horizontal condition on the movement block (51).

15 Claims, 11 Drawing Sheets

US 8,703,054 B2

DIRECTION SELECTION MECHANISM FOR ANALYTICAL TOOL, AND ANALYTICAL DEVICE

TECHNICAL FIELD

The present invention relates to a mechanism for supplying a plurality of analytical tools to a target location in manner such that the drop faces of the respective analytical tools, on which a drop of a sample is dispensed, face in the same direction, and also relates to analysis apparatus incorporating such a mechanism.

BACKGROUND ART

One type of urine analysis apparatus has a construction wherein urine analysis is conducted by extracting specimens one at a time from an accommodating unit where a plurality of specimens are accommodated and supplying these specimens continuously to a photometric unit. Usually a plurality of specimens are accommodated in the accommodating unit but there is no uniformity of arrangement as regards their front and rear faces. The analysis apparatus is therefore constructed to identify front and rear of specimens extracted from the accommodating unit and to supply the specimens to the photometric unit after putting the specimens in a uniform arrangement as regards front and rear on the basis of the results of this discrimination process (see for example Patent Document 1 and Patent Document 2).

As a method of putting the front and rear of the specimens in a uniform arrangement, in some cases a rotary body is utilised formed with through-holes for accommodating specimens (see for example Patent Document 3). In this method, the front and rear directions of the specimens are put in a uniform arrangement by controlling the direction of rotation of the rotary body in accordance with the results of identification of front or rear of the specimens by a sensor, after feeding the specimens extracted from the accommodating unit into the rotary body formed with through-holes.

However, in the method described above, due to the need to provide a rotary body of special shape and a mechanism for rotating this rotary body, the construction of the analysis apparatus becomes complicated, making the apparatus more bulky and tending to increase manufacturing costs. Furthermore, a drive source such as a dedicated motor is required for driving the rotary body, making the problems described above even more severe. Not only this, but running costs are also increased by the need to drive the dedicated motor.

Patent Document 1: JP-A-H07-306206
Patent Document 2: JP-B-H06-99018
Patent Document 3: JP-A-2000-35433

DISCLOSURE OF THE INVENTION

An object of the present invention is to supply analytical tools to a photometric location, with the orientation of the drop faces of the analytical tools being unified, without causing bulkiness of the apparatus or an increase in manufacturing costs, and while preventing rise in the running costs needed for conduction of the analysis.

According to a first aspect of the present invention, there is provided a mechanism for selecting the orientation of an analytical tool comprising: a passage along which a plate-shaped analytical tool is moved from above to below; and a movement block, made capable of reciprocatory movement in a horizontal direction including a first direction and a second direction constituting a direction opposite thereto, for moving the analytical tool incoming along the passage in the first direction, characterized by being constructed such that, in a condition in which the movement block has been brought to rest directly below the outlet of the passage, the incoming analytical tool that has moved through the passage is erected on the movement block and tipped over to be placed in a horizontal condition on the movement block by movement of the movement block in the first or second direction.

According to a second aspect of the present invention, there is provided analytical apparatus comprising: an accommodating section for accommodating a plate-shaped analytical tool; a passage for moving the analytical tool accommodated in this accommodating section from above to below; a drop dispensing section whence a drop of sample is dispensed onto the analytical tool; and a movement block, made capable of reciprocatory movement in a horizontal direction including a first direction toward the drop dispensing section and a second direction opposite thereto, for moving the analytical tool incoming along the passage towards the drop dispensing section, characterized being constructed such that, in a condition in which the movement block has been brought to rest directly below the outlet of the passage, the incoming analytical tool that has moved through the passage is erected on the movement block and tipped over to be placed in a horizontal condition on the movement block by movement of the movement block in the first or second direction.

A groove is provided for positioning the side face of an analytical tool, when for example the analytical tool is erected, in the movement block. Preferably the cross-section of this groove is V-shaped.

Preferably the movement block is constructed to have an erect face for preventing movement of the analytical tool in the second direction on this movement block when this movement block has moved in the first direction.

The analytical apparatus according to the present invention is constructed such that positional deviation of the analytical tool in the first and second directions in for example the drop dispensing section is corrected. Preferably the construction is such that positional deviation of the analytical tools is corrected by sandwiching the movement block between an erect face of the movement block and an erect face of the drop dispensing section when the analytical tool is positioned in the drop dispensing section.

In a preferred embodiment of the present invention, the analytical tool is erected on the movement block by engagement of one side edge thereof with the movement block while the other side edge engages an edge at the outlet side in the passage.

In a preferred embodiment of the present invention, the construction is such that, on the movement block, whether the drop face onto which a drop of sample is dispensed in the analytical tool is set to face upwards or downwards can be selected by selecting whether the movement block is moved in the first or second direction.

In a preferred embodiment of the present invention, the construction is such that there is further provided determination means utilised for determining which of the first direction or the second direction is faced by for example the drop face onto which a drop of sample is dispensed in the analytical tool when erected on the movement block. The determination means may be for example provided on a guide having the passage.

In a preferred embodiment of the present invention, the movement block is constructed to select whether the movement block is moved in the first direction from a condition in which the analytical tool has been erected or whether the movement block is moved in the first direction after movement in the second direction in accordance with the results of determination by the determination means.

DESCRIPTION OF THE PREFERRED EMBODIMENTS

Figure 1:
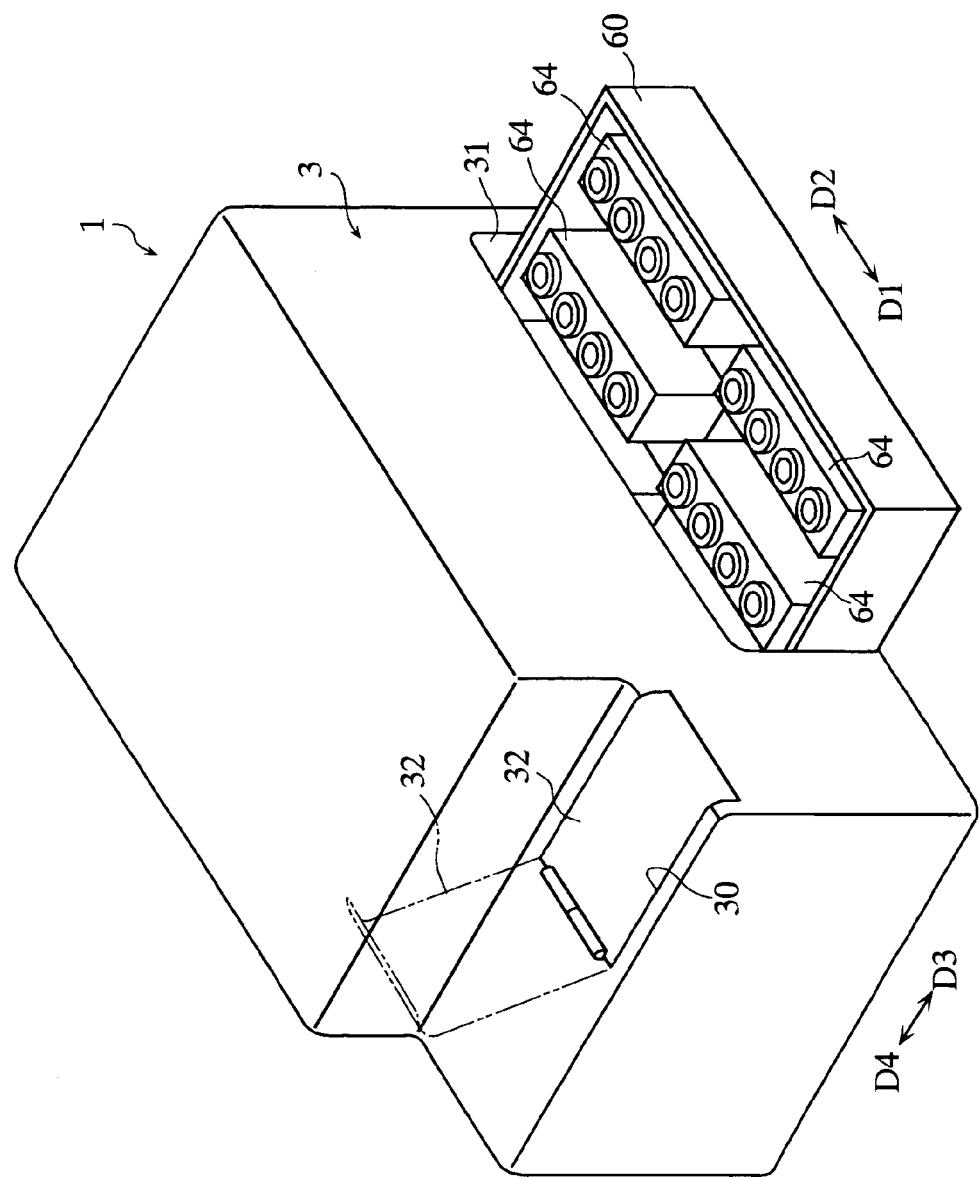
FIG. 1 is an overall perspective view showing an example of analytical apparatus according to the present invention.
Figure 2:
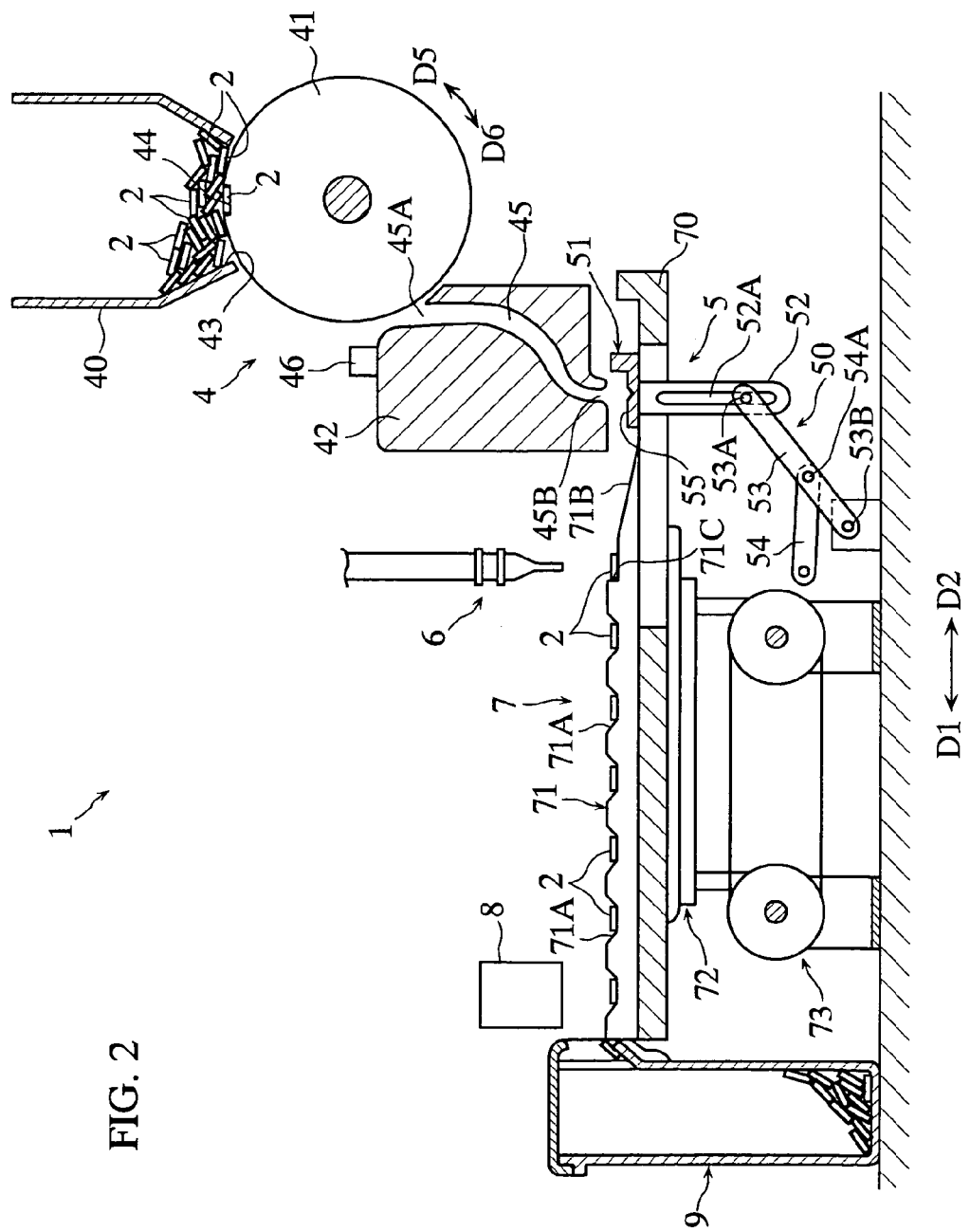
FIG. 2 is a cross-sectional view given in explanation of the internal structure of the analytical apparatus shown in FIG. 1.

The analytical apparatus 1 shown in FIG. 1 and FIG. 2 is constructed to automatically analyse a plurality of constituents in urine, using a specimen 2. As the specimens 2 used in this analysis apparatus 1, a plurality of reagent pads 21 are arranged on a short rectangular strip-shaped substrate 20 (see FIG. 3) adjacent to each other in the longitudinal direction of this substrate 20. The analytical apparatus 1 comprises a casing 3, specimen supply mechanism 4, sliding feed mechanism 5, sample supply mechanism 6, pitch feed mechanism 7, photometric mechanism 8 and discharge box 9.

As shown in FIG. 1, apertures 30, 31 are provided in the casing 3. The aperture 30 is employed (see FIG. 11) when inserting the discharge box 9 and opens in the upward direction. This aperture 30 is opened and closed by means of a lid 32 attached to the casing 3 and its aperture area is set to be smaller than the bottom wall 93E (see FIG. 9 to FIG. 11) of the discharge box 9, to be described. A lid 32 is rotatably attached to the casing 3 to be positioned above the casing 3 when the aperture 30 is open. In this way, when the aperture 30 is opened by opening the lid 32, the lid 32 cannot project to the front, rear or side of the casing 3. In contrast, the aperture 31 is provided at the front face of the casing 3 in order to permit insertion of racks 64 with respect to a rotation box 60, by exposing part of this rotation box 60, as will be described.

As shown in FIG. 2, the specimen supply mechanism 4 serves for supplying the specimens 2 one at a time to the sliding feed mechanism 5. This specimen supply mechanism 4 comprises an accommodating section 40, rotary drum 41 and guide 42.

The accommodating section 40 serves for accommodating a plurality of specimens 2 in a condition with their long axes directed in the D3, D4 directions (see FIG. 1 and FIG. 3), and comprises a lower aperture 43. This lower aperture 43 serves to expose the rotary drum 41 in the interior of the accommodating section 40. Specifically, the plurality of specimens 2 of the accommodating section 40 have the appearance of being stacked in the rotary drum 41.

The rotary drum 41 serves for continuously extracting specimens 2 from the accommodating section 40 and for moving the specimens 2 one at a time into the guide 42. This rotary drum 41 is rotated with a fixed angular velocity by control means, outside the Figure, arranged directly below the accommodating section 40 to permit rotation thereof in the direction D5 (anti-clockwise direction in the Figure), so that its axis lies in the directions D3, D4 (see FIG. 1 and FIG. 3). Recesses 44 extending in the axial direction (directions D3, D4 (see FIG. 1 and FIG. 3) are provided in the rotary drum 41. These recesses 44 are formed of dimensions such as to permit a single specimen 2 to be fitted therein. Specifically, the specimen 2 is moved in the direction D5 by rotation of the rotary drum 41 in the direction D5 when held in a recess 44 of the rotary drum 41. The specimen 2 that is held in the rotary drum 41 separates from the rotary drum 41 and falls down under its own weight when positioned at a location corresponding to the guide 42. Since the rotary drum 41 is rotated with angular velocity by control means outside the Figure, specimens 2 are successively extracted from the accommodating section 40 at fixed time intervals by the rotary drum 41 in the specimen supply mechanism 4.

It should be noted that in the specimen supply mechanism 4 the construction may be such that a specimen 2 that is held in a recess 44 may be scraped from the rotary drum 41 (recess 44) by means of a blade.

The guide 42 is provided with the purpose of directing specimens 2 to the movement block 51 of the sliding feed mechanism 5, to be described, after they have been extracted and moved by the rotating drum 41. This guide 42 comprises a passage 45 for defining the movement path of the specimens 2. This passage 45 is constructed such that a specimen 2 introduced from the inlet 45A is discharged from the outlet 45B without being inverted as to front and rear. Accordingly, the outlet 45B of the passage is arranged in a position (see FIG. 5) where the distance H between this and the carrying face 55 on the movement block 51 is shorter than the dimension (width dimension) in the short axis direction of the specimen 2 when the movement block 51, to be described, is positioned directly below the outlet 45B.

A sensor 46 is provided on this guide 42 in the vicinity of the inlet 45A of the passage. This sensor 46 is provided with the purpose of identifying front and rear of the specimen 2 held in the recess 44 of the rotary drum 41. Specifically, the sensor 46 serves to determine whether the reagent pad 21 (see FIG. 3) of the specimen 2 is facing outwards in the radial direction of the rotary drum 41 (i.e. whether it is front-facing), or whether the reagent pad 21 of the specimen 2 is facing inwards in the radial direction (i.e. whether it is rear-facing) when a recess 44 is positioned in a location corresponding to that of the guide 42. For example a reflective type photosensor could be employed as the sensor 46. In this case, front and rear of the specimen 2 can be identified by monitoring the amount of reflected light detected by the reflective type photosensor.

It should be noted that the sensor 46 could be incorporated within the guide 42 to make it possible to identify front and rear of the specimen 2 whilst the specimen 2 is moving along the passage 45, or could be positioned in a location adjacent to the accommodating section 40, to make it possible to identify front and rear of the specimen 2 immediately after extraction thereof from the accommodating section 40.

Figure 3:
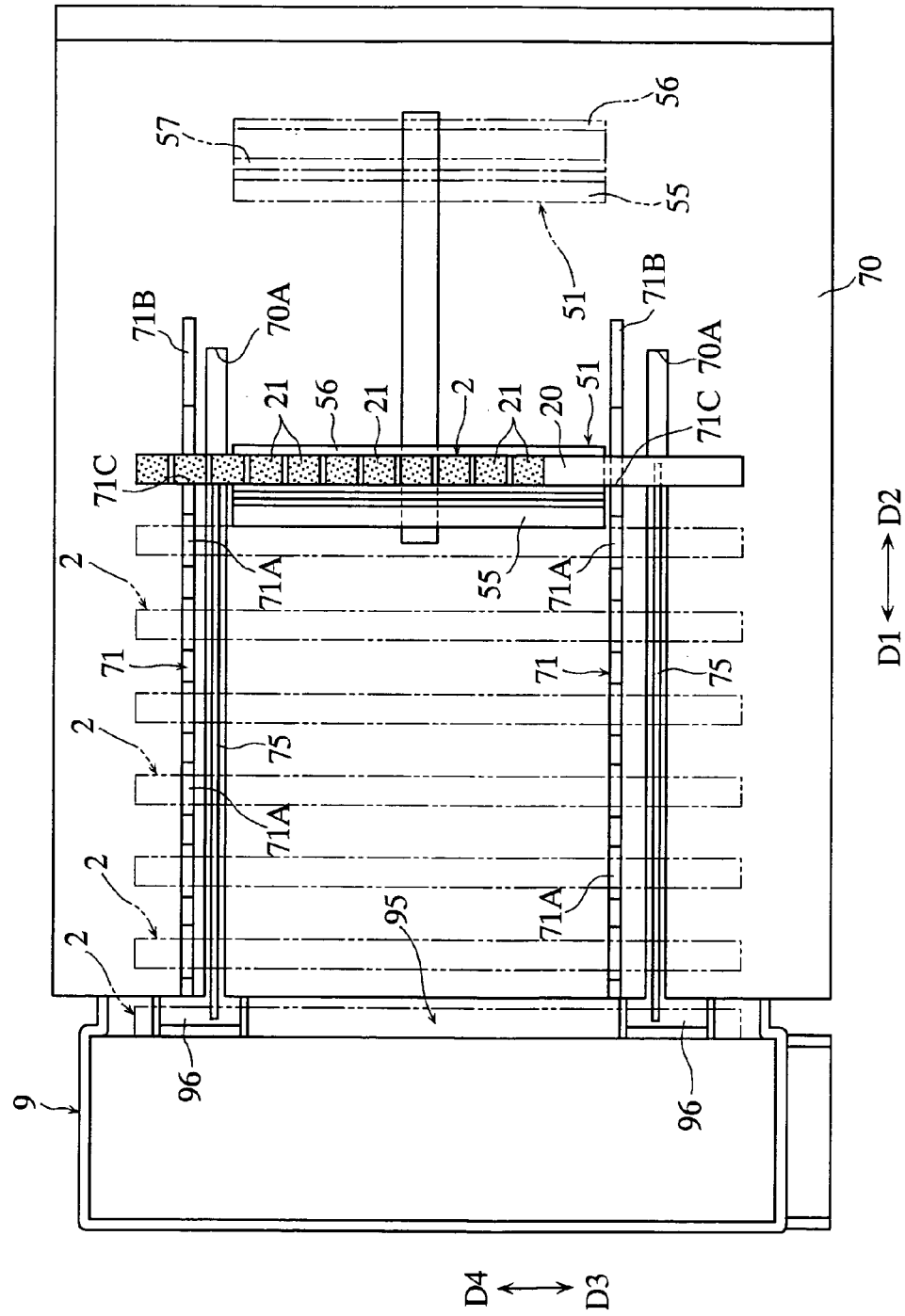
FIG. 3 is a plan view showing a detail given in explanation of the internal structure of the analytical apparatus shown in FIG. 1.
Figure 4:
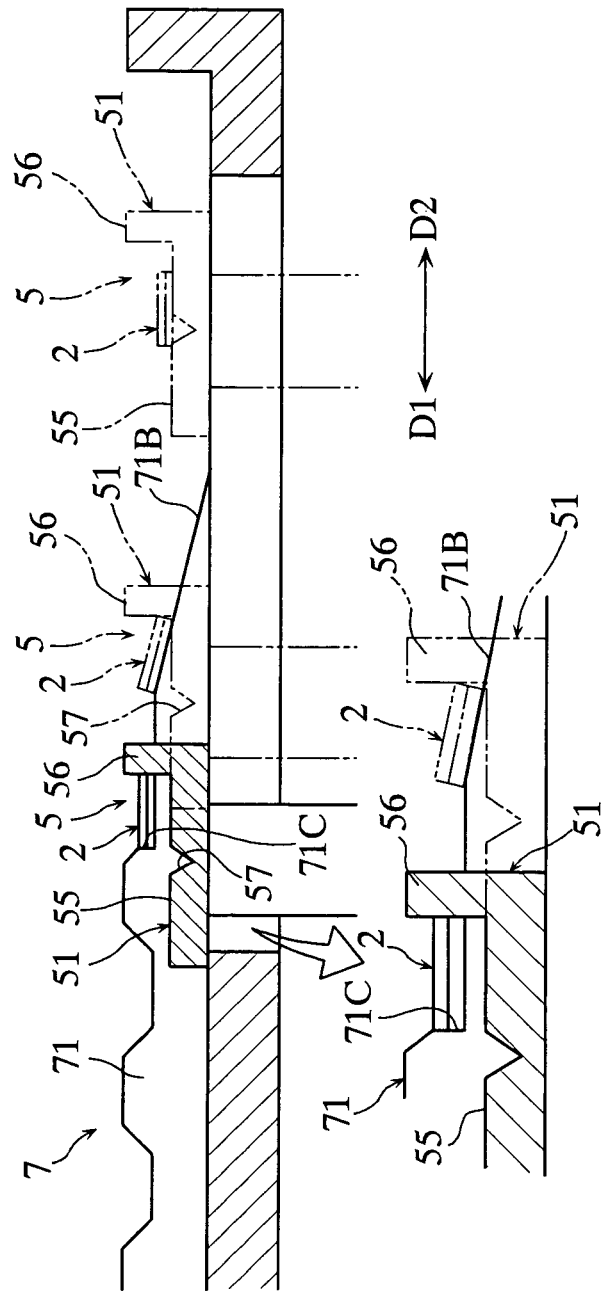
FIG. 4 is a cross-sectional view showing a detail given in explanation of the operation of the movement block of the sliding feed mechanism and a detail of the pitch feed mechanism in the analytical apparatus shown in FIG. 1.

As shown in FIG. 2 to FIG. 4, the sliding feed mechanism 5 is provided with the purpose of feeding a specimen 2 that has been supplied by the specimen supply mechanism 4 to a drop dispensing position (end on the side D2 on the rail 71 of the pitch feed mechanism 7, to be described) whence reagent can be supplied by the reagent supply mechanism 6. This sliding feed mechanism 5 further comprises a function of aligning the direction (front/rear) of the specimens 2 that are continuously supplied by the specimen supply mechanism 4 and of correcting the orientation of the specimens 2 when the specimens 2 are moved by the pitch feed mechanism 7. This sliding feed mechanism 5 comprises a drive mechanism 50 and movement block 51.

As shown in FIG. 2, the drive mechanism 50 is provided with the purpose of moving the feed block 51 in the direction D1 or D2 on the feed table 70 of the pitch feed mechanism 7, to be described. This drive mechanism 50 is constructed as a link mechanism and comprises a fixed arm 52 and movable arms 53, 54. The fixed arm 52 is fixed with respect to the movement block 51 and comprises a through-hole 52A extending in the vertical direction. The movable arm 53 is linked to the fixed arm 52 by means of a shaft 53A capable of movement through the through-hole 52A and is linked to be capable of movement with respect to the casing 3 by means of the shaft 53B. The movable arm 54 is rotatably linked with the movable arm 53 by means of the shaft 54A and is made capable of movement parallel with the directions D1, D2 by means of a mechanism outside the Figure.

In this drive mechanism 50, when a force is applied to the movable arm 54 towards the direction D1, the shaft 53A moves upwards through the through-hole 52A of the fixed arm 52 and the movable arm 53 rotates in the D5 direction (anti-clockwise direction in the Figure) and the fixed arm 52 (movement block 51) is moved in the D1 direction. On the other hand, when force acts on the movable arm 54 in the D2 direction, the shaft 53A is moved downwards through the through-hole 52A of the fixed arm 52, resulting in the movable arm 53 rotating in the D6 direction (clockwise direction in the Figure) and the fixed arm 52 (movement block 51) being moved in the D2 direction. Specifically, operation is effected such that, when the drive mechanism 50 is to move the movement block 51 in the D1 direction, the movable arm 54 is moved in the D1 direction, whereas, when the movement block 51 is to be moved in the D2 direction, the movable arm 54 is moved in the D2 direction. Drive of the movable arm 54 is controlled by for example control means, outside the Figure.

However, the drive mechanism for moving the movement block 51 is not restricted to the mechanism described above and drive mechanisms of other construction could be employed.

Figure 5:
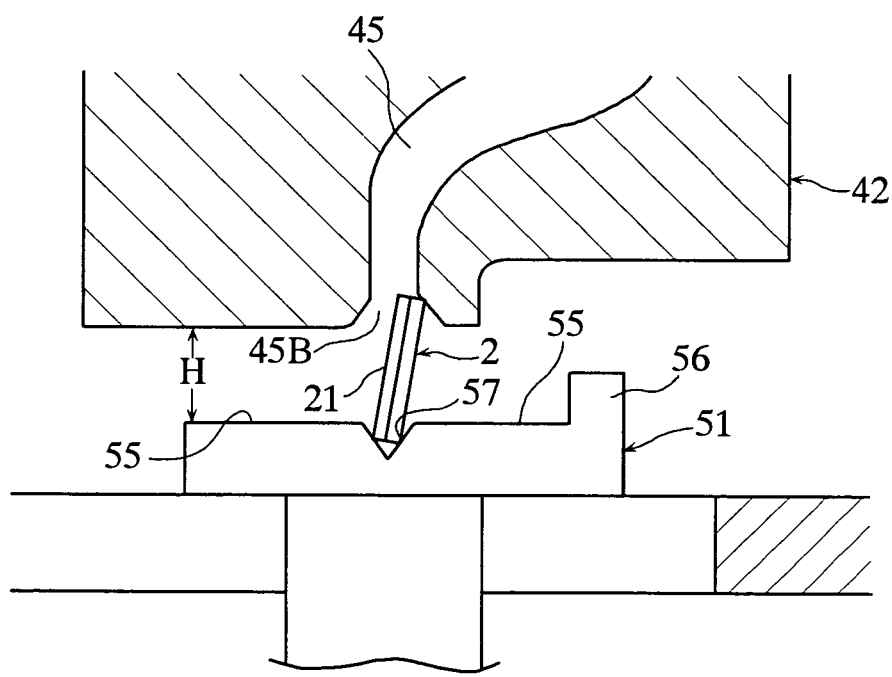
FIG. 5 is a cross-sectional view showing the specimen supply mechanism and a detail of the sliding feed mechanism in the analytical apparatus shown in FIG. 1.

As shown in FIG. 3, the movement block 51 has a fixed length dimension in the D3 and D4 directions to be capable of carrying a specimen 2 supplied by the specimen supply mechanism 4 (see FIG. 2) such that its long axis lies in the D3 or D4 direction. The dimensions in the D3 and D4 directions in the movement block 51 are set to be smaller than the interval in the D3, D4 directions of the pair of rails 71 in the pitch feed mechanism 7, to be described. As shown in FIG. 3 and FIG. 5, this movement block 51 comprises a carrying face 55 and an erect wall 56.

The carrying face 55 serves for carrying a sample 2 and its dimension in the D3, D4 directions is larger than in the D1, D2 directions. And the dimension in the D3, D4 directions of the carrying face 55 is set to be larger than the width dimension (dimension in the short axis direction) of the specimen 2. The carrying face 55 is formed with grooves 57 extending in the D3, D4 directions in substantially the middle in the D1, D2 directions. These grooves 57 serve for engagement with one side edge of a specimen 2 when the specimen 2 is discharged from the outlet 45B of the passage 45 in the guide 42, and are formed with V-shaped cross-section.

As shown in FIG. 5, the distance H of the outlet 45B of the passage 45 in the guide 42 with respect to the carrying face 55 is set to be smaller than the width dimension of the specimen 2, as described above. Consequently, a specimen 2 that is discharged from the outlet 45B engages the groove 57 with one of its side edges and engages the outlet 45B with the other of its side edges. As a result, the specimen 2 is in an erect condition when it is discharged from the outlet 45B. It should be noted that, since, in the passage 45 of the guide 42, the specimen 2 is moved without being inverted as to front and rear, if the reagent pad 21 in the recess 44 of the rotary drum 41 was directed outwards in the radial direction, the specimen 2 is erected (see FIG. 6A) with its reagent pad 21 facing substantially the D1 direction in the movement block 51. Contrariwise, if the reagent pad 21 was facing inwards in the radial direction in the recess 44, the specimen 2 is erected (see FIG. 6B) with its reagent pad 21 facing substantially in the direction D2 in the movement block 51.

Figure 6A:
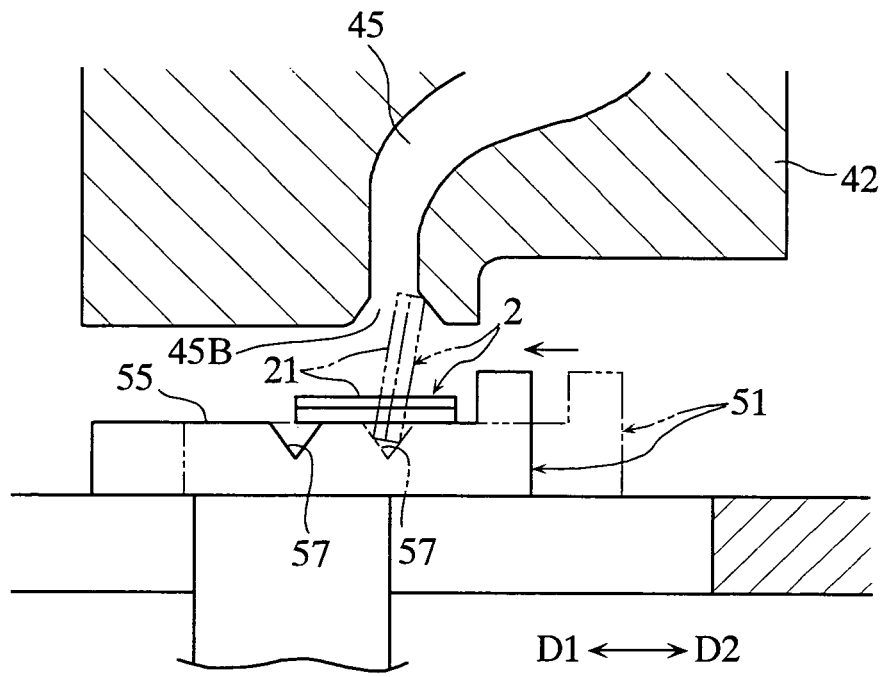
FIG. 6 is a cross-sectional view corresponding to FIG. 5 given in explanation of the operation of the sliding feed mechanism.
Figure 6B:
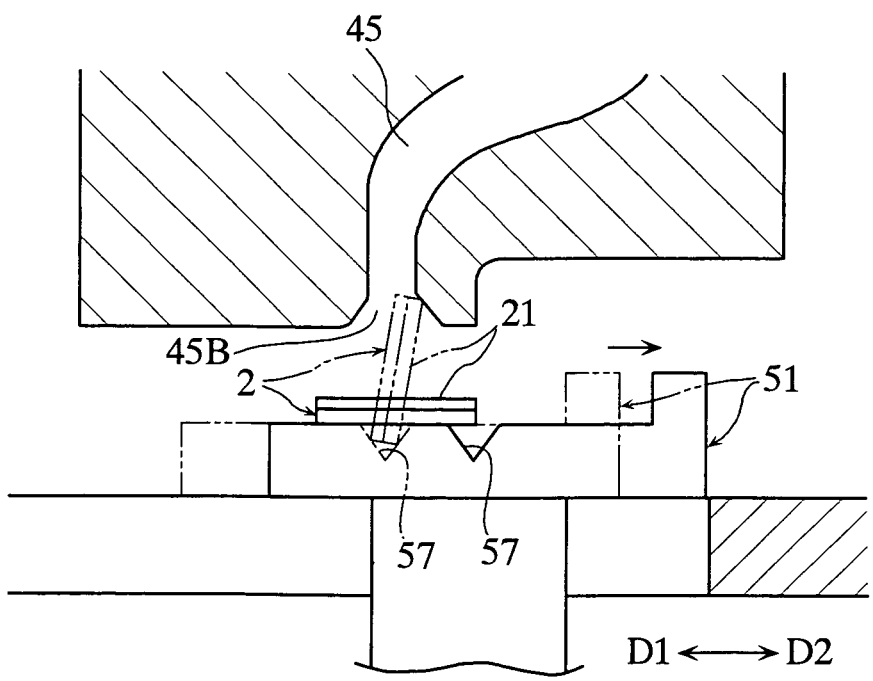

As shown in FIG. 6A and FIG. 6B, the specimen 2 in the erect condition is tipped over by movement in the D1 or D2 direction along the movement pad 51, with the result that the reagent pad 21 is placed on the carrying face 55 to face upwards. More specifically, as shown in FIG. 6A, when the specimen 2 is erected such that the reagent pad 21 substantially faces D1, the movement block 51 is moved in the D1 direction. In this way, the specimen 2 is tipped over by relative movement in the D1 direction of the side edge that is positioned below further than the side edge that is positioned above, with the result that the reagent pad 21 assumes an upwardly facing condition. In contrast, as shown in FIG. 6B, when erected such that the reagent pad 21 of the specimen 2 substantially faces D2, the movement block 51 is moved in the D2 direction. In this way, the specimen 2 is tipped over so that the reagent pad 21 assumes an upwardly facing orientation, by causing the side edge positioned below to be moved relatively further in the D2 direction than the side edge positioned above.

As described above, one side edge of the specimen 2 that has been erected on the carrying face 55 is engaged with the groove 57. Consequently, when the movement block 51 is moved in the D1 or D2 direction from a position directly below the outlet 45B of the passage 45, this side edge can be reliably moved together with the movement block 51 without the one side edge of the specimen 2 sliding on the carrying face 55.

The cross-sectional shape of the groove 57 is not restricted to being V-shaped so long as it is of shape permitting engagement with the side edge of the sample, and another shape could be adopted such as for example a U-shape or rectangular shape. Also, a construction could be adopted wherein the grooves 57 are dispensed with and the side edge of a sample is engaged by generating sufficient frictional resistance between one of the side edges of the specimen 2 and the carrying face 55, by making the surface of the carrying face 55 a rough face.

The direction of the reagent pad 21 of the erected specimen 2 on the carrying face 55 of the movement block 51 is determined in accordance with the result of the detection by the sensor 46. Specifically, since movement of the specimen 2 in the passage 45 of the guide 42 takes place without front/rear inversion, the direction of the reagent pad 21 in the recess 44 of the rotary drum 41 and the direction of the reagent pad 21 of the erected specimen 2 on the carrying face 55 of the movement block 51 correspond with each other. Consequently, it is possible to ascertain the direction of the reagent pad 21 of the specimen 2 erected on the carrying face 55 by determining the direction of the reagent pad 21 in the specimen 2 accommodated in the recess 44. As a result, in the sliding feed mechanism 5, it can be arranged that the direction of the reagent pad 21 of the specimens 2 that are successively placed on the carrying face 55 is always upwards, by moving the movement block 51 in the D1 or D2 direction in accordance with the result of detection by the sensor 46.

As described above, the sliding feed mechanism 5 is constructed to make it possible to unify the direction of the reagent pads 21 of the specimens 2 that are successively supplied, instead of simply performing feeding of the specimens 2. Specifically, in the analytical apparatus 1, it is unnecessary to provide a mechanism for unifying the directions of the reagent pads in the samples separately from the mechanism for feeding the specimens 2, as was done conventionally, so increase in size of the analytical apparatus 1 and increase in running costs can be suppressed.

As shown in FIG. 3 and FIG. 4, an erect wall 56 is provided in order to suppress movement of the specimen 2 in the direction D2 when the movement block 51 is moved in the direction D1 in a condition with a specimen 2 placed on the carrying face 55. In this way, when the specimen 2 is moved in the D1 direction by the movement block 51, it is possible to prevent separation of the specimen 2 from the movement block 51 in the D2 direction. In addition, the erect wall 56 has the role of correcting the orientation of the specimen 2 in the D1 and D2 directions by gripping the specimen 2 between the erect faces 71C of the pair of rails 71 in the pitch feed mechanism 7 when the movement block 51 is fed to the drop dispensing position referred to above.

Figure 7:
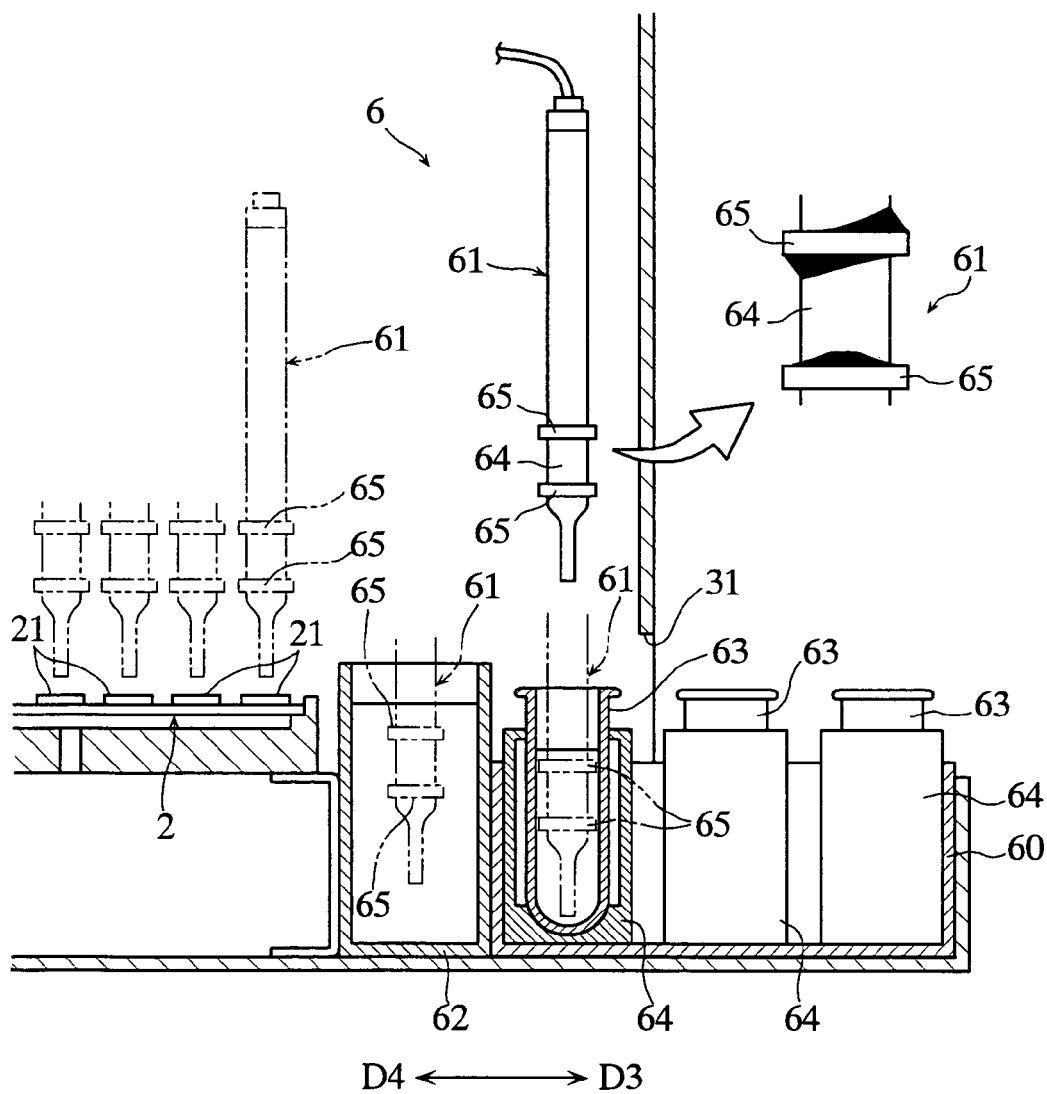
FIG. 7 is a cross-sectional view showing a detail given in explanation of the specimen supply mechanism in the analytical apparatus shown in FIG. 1.

As shown in FIG. 7, the sample supply mechanism 6 serves for dispensing of a drop of reagent in respect of the reagent pads 21 of the specimens 2, in the above drop dispensing position. This reagent supply mechanism 6 comprises a rotation box 60, nozzle 61 and washing tank 62.

The rotation box 60 serves for supporting a plurality of racks 64 for holding test-tubes 63 in rotatable fashion. Specifically, the rotation box 60 is constructed to enable successive movement of the test-tube 63 that are the subject of testing on the movement track of the nozzle 61, by rotation of the plurality of racks 64.

The nozzle 61 collects sample from the test-tube 63 in a prescribed position and serves for dispensing of a drop thereof onto the reagent pad 21 of a specimen 2 which is in the drop dispensing position, and is accordingly capable of movement in the D3 and D4 direction and in the vertical direction. This nozzle 61 is connected with a pump, outside the Figure, and is constructed to make possible the application of suction force and discharging force to the interior of the nozzle 61. Two annular projections 65 are provided at the tip 64 of the nozzle 61. These annular projections 65 serve to prevent excess sample adhering to the tip 64 of the nozzle 61 from dripping when a drop of sample is dispensed onto the reagent pad 21. The annular projections 65 are mounted in a positions that are immersed in the sample held in a test-tube 63 when the tip 64 of the nozzle 61 is inserted in the test-tube 63. The annular projections 65 may be formed for example by surrounding the tip 64 of the nozzle 61 with ring-shaped member. For example members obtained by cutting a tube made of polymer in the radial direction may be employed as the ring-shaped members. Such annular projections 65 can be obtained easily and at low cost, so the beneficial effect of preventing dripping of sample can be obtained without significant adverse effects on costs or ease of operation.

It should be noted that the annular projections 65 could be integrally built into the tip of the nozzle 61, and, regarding the number thereof, a single projection or three or more could be employed.

The washing tank 62 holds washing liquid such as distilled water or a buffer solution and serves for washing the tip 64 of the nozzle 61 after completion of supply of sample in respect of a single specimen 2.

When collecting a sample in the sample supply mechanism 6, first of all the tip of the nozzle 61 is inserted in the target test-tube 63. The nozzle 61 is inserted in the test-tube 63 as far as a position in which the two annular projections 65 are immersed in the sample held in the test-tube 63. Next, the sample is held in the interior of the tip 64 of the nozzle 61 by applying suctional force to the interior of the nozzle 61.

When sample is supplied to the specimen 2 in the sample supply mechanism 6, first of all, the tip 64 of the nozzle 61 is raised from the test-tube 63. At this point, thanks to the annular projections 65 at the tip 64 of the nozzle 61, excess sample adhering to the surface of the tip 64 of the nozzle 61 is held in a condition adhering to the annular projections 65 by surface tension of the sample. In FIG. 7, excess sample adhering to the annular projections 65 is indicated by black shading at the expanded portion of the nozzle 61. Next, the nozzle 61 is successively moved to locations corresponding to the reagent pads 21 and a drop of sample is dispensed to each reagent pad 21 by applying discharging force to the interior of the nozzle 61 at the timing with which the tip of the nozzle 61 is facing the reagent pad 21. At this point, sample adhering to the surface of the tip 64 in the nozzle 61 is maintained in a condition adhering to the annular projections 65, so dripping from the nozzle 61 is suppressed. As a result, dripping of sample from the nozzle 61 when a drop of sample is dispensed to the reagent pad 21 at the nozzle 61 can be prevented. In this way, the amount of sample to be dispensed as a drop at the reagent pad 21 can be made to be the target amount, so a drop in degree of accuracy of analysis caused by inexactness of the amount of drop dispensation can be suppressed. Since such benefits are obtained merely by appropriate design of the shape of the tip 64 of the nozzle 61, there are no points of alteration to the construction other than the nozzle, so there is no question of the analytical apparatus 1 becoming bulky.

When supply of sample to the specimen 2 is completed, the tip 64 of the nozzle 61 including the annular projections 65 is washed by immersing the tip 64 of the nozzle 61 in the washing solution held in the washing tank 62. Excess reagent adhering to the annular projections 65 of the nozzle 61 is thereby removed. As a result, in successively performed supply of sample, contamination of the tip 64 of the nozzle 61 by previous solutions is suppressed, and, since a washing solution is employed for the removal of the excess sample, there is no need to employ consumable products such as filter paper, which is beneficial from the point of view of assay costs.

Figure 8:
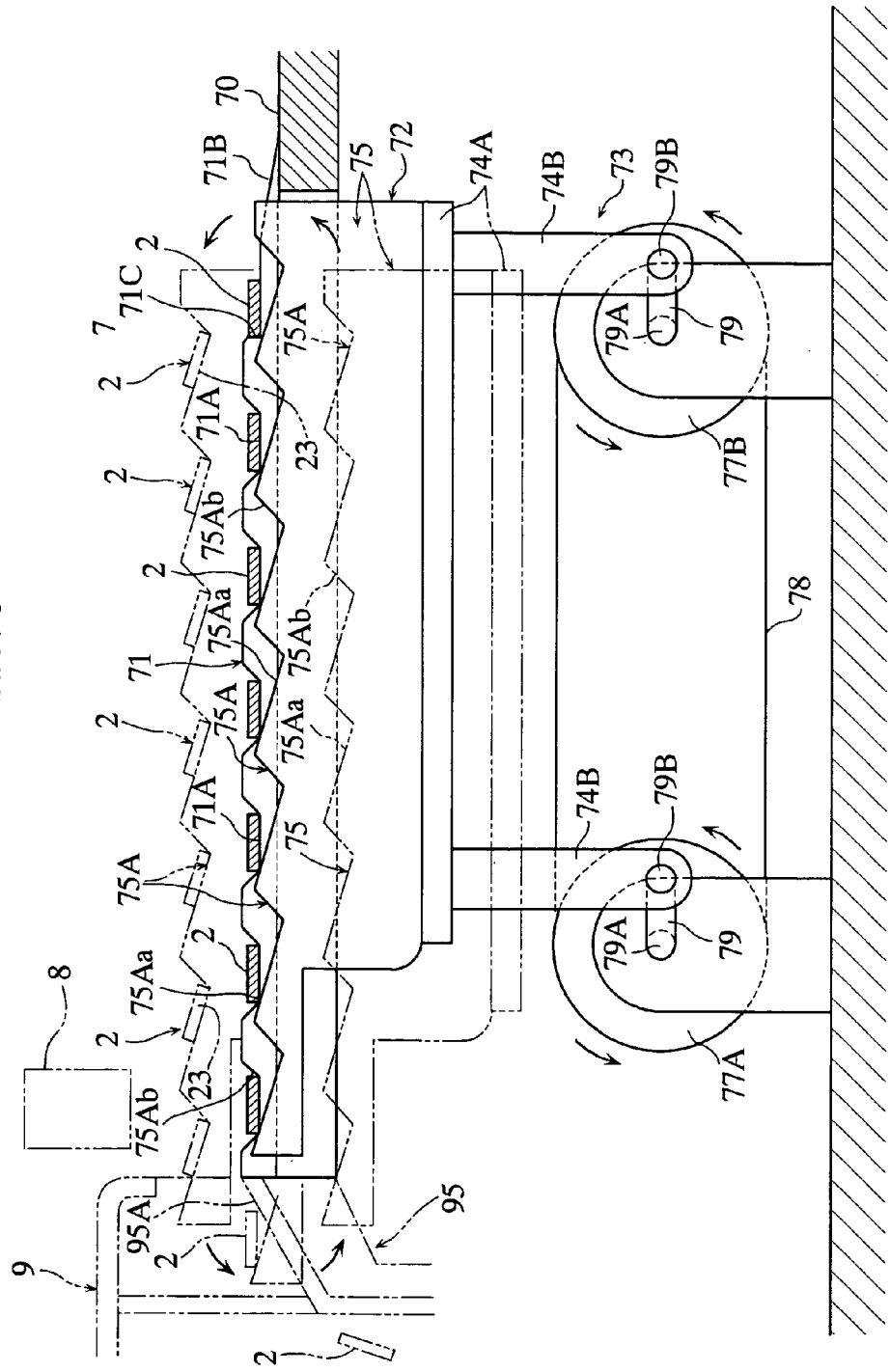
FIG. 8 is a cross-sectional view showing a detail given in explanation of the pitch feed mechanism whereof a detail is shown in FIG. 4.

As shown in FIG. 2, FIG. 3 and FIG. 8, the pitch feed mechanism 7 serves for feeding specimens 2 fed by the sliding feed mechanism 6 to the position where photometry can be effected in the photometric mechanism 8 and for causing the specimens 2 to be accommodated in the discharge box 9 after completion of photometry. This pitch feed mechanism 7 comprises a feed table 70, a pair of rails 71, a feed member 72 and a drive mechanism 73.

The feed table 70 defines the feed region and serves for holding the pair of rails 71. This feed table 70 is provided with a pair of slits 70A. The pair of slits 70A serve for permitting rotary movement of carrying elements 75 on the feed member 72, to be described, and extend in the directions of the arrows D1, D2 in a condition having a certain mutual interval.

The pair of rails 71 serve to support a specimen 2 and are formed to extend in the D1, D2 directions, separated by a certain interval in the direction of the arrows D3, D4. Each rail 71 is provided with a plurality of recesses 71A arranged in the D1, D2 direction in the Figure. The plurality of recesses 71A are arranged at a certain interval in the D1, D2 direction on the rails 71A and a specimen 2 is supported on this pair of rails 71 in a condition parallel with the D3, D4 directions. An inclined face 71B and erect face 71C are provided as best shown in FIG. 4 and FIG. 8 at the end of the pair of rails 71 on the D2 side. The inclined face 71B serves for displacing upwards the position A of an incoming specimen 2 fed by the sliding feed mechanism 5 in the vertical direction. Specifically, a gap is formed between a specimen 2 and the carrying face 55 of the movement block 51 while the specimen 2 is being moved over the inclined face 71B. In this way, when the movement block 51 is caused to move in the D2 direction, the movement block 51 can move away from the specimen 2. On the other hand, the erect face 71C serves for restricting the movement of the specimen 2 in the D1 direction, and for gripping the specimen 2 between itself and the erect wall 56 of the movement block 51. In this way, the orientation of the specimen 2 in the D1, D2 directions is corrected. However, correction of the orientation of the specimen 2 in the D1, D2 directions could also be achieved by providing an element exhibiting the same functions as the erect face 71C on the feed table 70, separately from the rails 71.

As shown in FIG. 3 and FIG. 8, the feed member 72 serves for sequential pitch feeding of the specimen 2 placed on a specific recess 71A on the pair of rails 71 to an adjacent recess 71A. This feed member 72 is constituted to perform circular movement by means of a drive mechanism 73, to be described. The feed member 72 comprises two pairs of linking arms 74B (one pair in the Figure) that project downwards from the supporting plate 74A and a pair of carrying elements 75 that project upwards from the support plate 74A. The pair of carrying elements 75 are arranged to extend in the D1 and D2 directions in a condition separated by an interval in the D3, D4 directions on the supporting plate 74A. The carrying elements 75 comprise a plurality of recesses 75A arranged in the D1, D2 directions. As shown in FIG. 8, the recesses 75A in each carrying elements 75 are defined by a pair of inclined faces 75Aa, 75Ab, so that a specimen 2 is fed in a condition with the bottom face 23 of the specimen 2 in contact with the inclined face 75Aa. Specifically, the specimen 2 supported on the recess 71A of the rail 71 is raised in a condition supported by the inclined face 75Aa when the specimen 2 passes the portion corresponding to the recess 71A of the rail 71 with the recess 75A of the carrying elements 75 directed upwards from below. In contrast, when a specimen 2 supported on the inclined face 75Aa passes the portion corresponding to the recess 71A of the rail 71 with the recess 75A of the carrying elements 75 directed downwards from above, the specimen 2 is loaded onto the recess 71A from the inclined face 75Aa. By repeating this operation of raising and loading the specimens 2 in this way, the specimens 2 are successively moved into adjacent recesses in the D1 direction.

The drive mechanism 73 serves for rotary movement of the feed member 72. This drive mechanism 73 comprises two pairs of pullies 77A, 77B (one pair in the Figure) making a total of four pullies 77A, 77B that are rotated by a drive source (for example a motor) outside the Figure. In each of the pulley pairs 77A, 77B pullies 77A, 77B are connected by an endless belt 78. Each of the pulley pairs 77A, 77B are mutually arranged with an interval in the D3, D4 directions (see FIG. 1 and FIG. 3), although not shown in the Figure. The pullies 77A, 77B are fixed with respect to the linking arm 74B by means of a linking member 79. The linking member 79 comprises a pair of shaft sections 79A, 79B that are mutually offset in position, being rotatably fixed at these shaft sections 79A, 79B with respect to the linking arm 74B and the pulley 77A. In the drive mechanism 73 that is thus constituted, the pullies 77A are rotated in the same direction by a drive source (not shown) and the turning force of these pullies 77A acts as a force for rotating the linking arm 74B (feed member 72) i.e. carrying elements 75.

However, a cam mechanism or other type of mechanism could be adopted as the drive mechanism for circular movement of the feed member 72. Also, movement of the specimens 2 in the feed table 70 could be arranged to be performed by means of a feed arm, or could be arranged to be performed by means of a sliding feed mechanism 5, ensuring a large reciprocatory stroke of the movement block 51 in the sliding feed mechanism 5.

The photometric mechanism 8 shown in FIG. 2 serves for obtaining information corresponding to the degree of coloration of the reagent pads 21 by photodetection of the reflected light when light is directed onto the reagent pads 21 of the specimens 2. This photometric mechanism 8 comprises a light-emitting section omitted in the Figure and a photodetector section 72 and is capable of performing reciprocatory movement in the D3, D4 directions (see FIG. 1 and FIG. 3). The light-emitting section is capable of emitting light having for example a specified peak wavelength and is constituted by an LED. In contrast, the photodetector section serves for photodetection of light that is reflected from the reagent pads 21 and is constituted by for example a photodiode.

In the photometric mechanism 8, reflected light from the plurality of reagent pads 21 is continuously detected by the photodetection section, by directing the light onto the reagent pads 21 by means of a light emission section, while moving the photometric mechanism 8 in the D3, D4 directions (see FIG. 1 and FIG. 3) along the row of reagent pads 21 of the specimens 2. The photodetection results at the photodetector section form the basis used for calculation when analysis of the samples is conducted.

Figure 9:
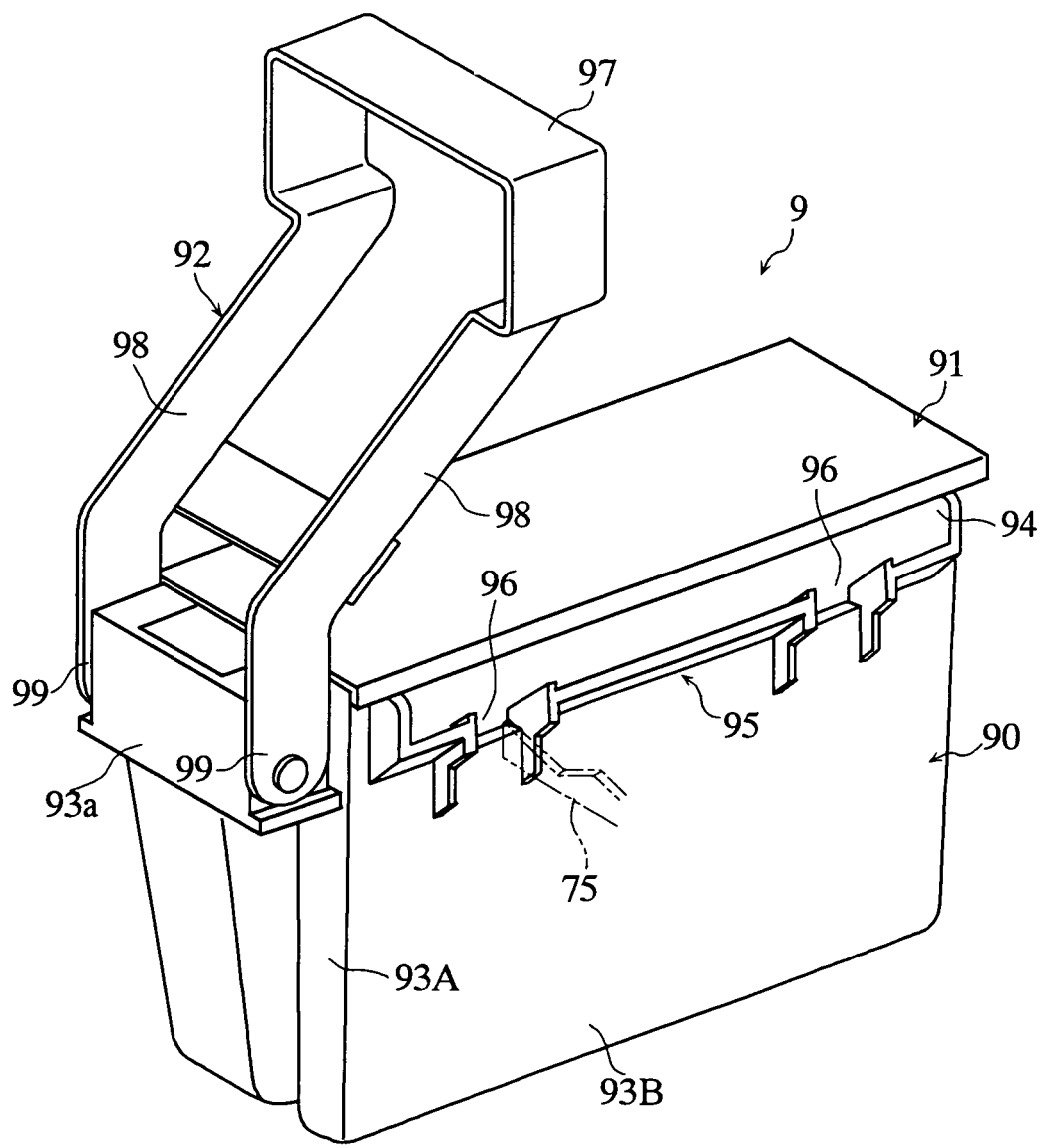
FIG. 9 is an overall perspective view of a discharge box in the analytical apparatus shown in FIG. 1.
Figure 10:
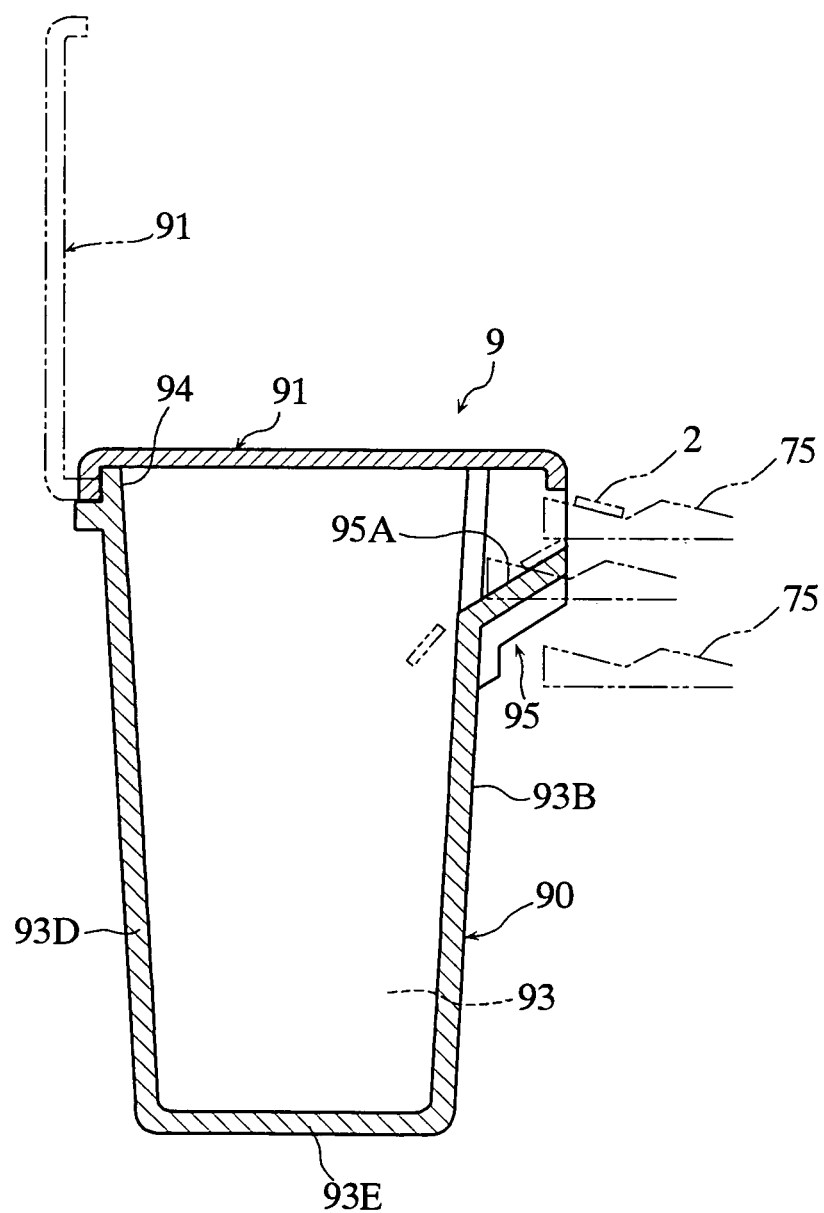
FIG. 10 is a cross-sectional view of the discharge box shown in FIG. 9.
Figure 11:
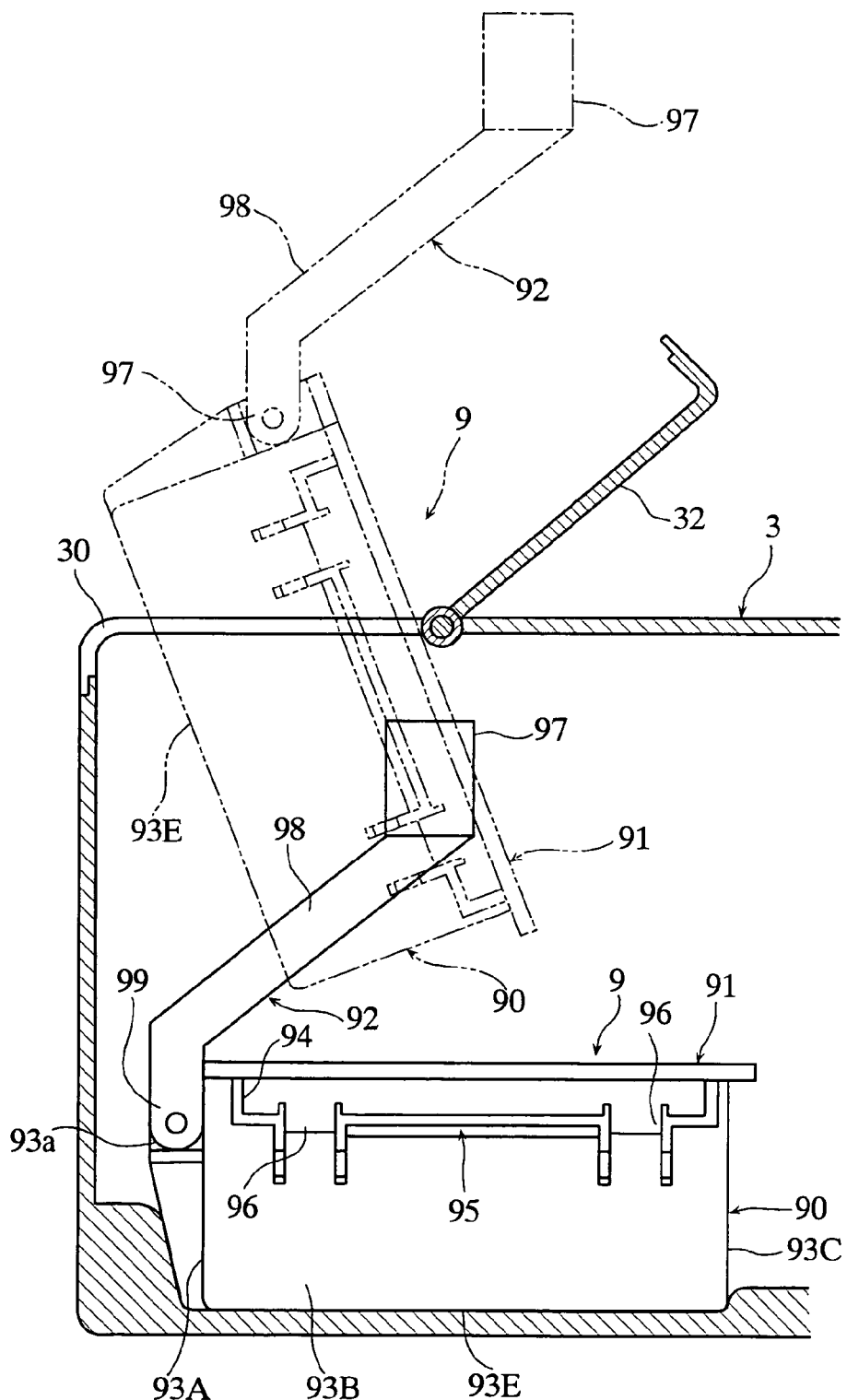
FIG. 11 is a cross-sectional view showing a detail given in explanation of the operation of the discharge box shown in FIG. 9.

As shown in FIG. 9 to FIG. 11, the discharge box 9 serves for accommodating specimens 2 whose photometry has been completed and is provided adjacent to the D1 side of the pitch feed mechanism 7. This discharge box 9 is capable of being removed or inserted through an aperture 30 of the casing 3 and comprises a main body 90, lid 91 and handle 92.

The main body 90 comprises a space 93 for accommodating specimens 2 defined by sidewalls 93A to 93D and a bottom wall 93E and an upper aperture 94. At the top of the sidewall 93A, there is provided a mounting section 93a for fixing a handle 92, that projects to the outside. The height dimension of the sidewall (sidewall adjacent to the pitch feed mechanism 7) 93B is made smaller than that of the other side walls 93A, 93C, 93D. An inclined section 95 projecting upwards in inclined fashion towards the outside of the main body section 90 is provided on the side wall 93B. Specifically, the inclined section 95 is formed such that the height of its upper face 95A is smaller in the D1 direction. This inclined section 95 functions (see in particular FIG. 8 and FIG. 10) as a guide for directing specimens 2 moved from the photometric location by the carrying elements 75 of the feed member 72 into the space 93 of the main body 90. A pair of recesses 96 are provided with a fixed interval on the inclined section 95. This pair of recesses 96 serve to allow rotary movement of the end of the carrying elements 75. Specifically, as shown in FIG. 3, FIG. 8 and FIG. 10, when the end of the carrying elements 75 moves the recesses 96 from above to below, the specimen 2 that is supported to bridge the pair of carrying elements 75 interferes with the upper surface 95A of the inclined section 95. As a result, while the carrying elements 75 move relatively downwards with respect to the specimen 2, the specimen 2 is supported on the upper face 95A of the inclined section 95. As described above, the upper face 95A of the inclined section 95 is formed such that its height becomes smaller in the D1 direction, so a specimen 2 placed on the upper face 95A of the inclined section 95 slides down the upper face 95A of the inclined section 95 due to its own weight, and is accommodated in the interior of the main body 90.

As shown in FIG. 9 to FIG. 11, the lid 91 serves for closing the upper aperture 94 of the main body 90 and is freely rotatably fixed with respect to the main body 90. As described above, the height dimension of the side wall 93B of the main body 90 is made smaller than that of the other side walls 93A, 93C, 94D. Consequently, in a condition in which the upper aperture 94 of the main body 90 is closed by the lid 91, a gap is formed between the top of the sidewall 93B (inclined section 95) and the lid 91. As can also be anticipated from the description given above, this gap constitutes an inlet for the accommodation of specimens 2 in the discharge box 9.

As shown in FIG. 9 and FIG. 11, the handle 92 is a portion that is utilised by the user when moving the discharge box 9, such as for example when removing or inserting the discharge box 9 with respect to the casing 3, and comprises a grip section 97 and a pair of bent arms 98. The grip section 97 is a portion for the purpose of gripping by a user when the discharge box 9 is to be moved. The bent arms 98 serve for fixing the handle 92 on the main body 90 and are provided for the purpose of defining the position of the grip section 97. The bent sections 98 extend from the grip section 97 and are rotatably journalled in the mounting section 93a of the main body 90 at the ends 99 thereof. Specifically, the entire handle 92 is rotatable about the journalled portion as a fulcrum and the relative position of the grip section 97 with respect to the main section 90 is defined by rotating the handle 92.

As shown in FIG. 11, the ends 99 of the bent arms 98 are arranged to interfere with the sidewall 93A when the grip section 97 is rotated in the direction such as to approach the lid 91. Specifically, the construction is such that the discharge box 9 can maintain an attitude in which the handle 92 is folded up, in a condition with the grip sections 97 positioned above the lid 91. Consequently, the discharge box 9 can be accommodated in the interior of the casing 3 without excessive increase in the volume thereof, thanks to the folding up of the handle 92. As a result, there is no need to secure a large space for the handle 92 in the interior of the casing 3. Also, if the discharge box 9 is accommodated in the interior of the casing 3 in a condition with the grip sections 97 positioned above the lid 91, the grip sections 97 are exposed through the aperture 30 in positions in which they are easily gripped by a user in a condition with the aperture 30 opened by opening the lid 32 of the casing 3. In this way, extraction of the discharge box 9 from the interior of the casing 3 is facilitated.

The mounting section 93a of the main body 90 is provided above the sidewall 93A of the main body 90 as described above. Consequently, the handle 92 are linked with the main body 90 at the corners of the main body 90. As a result, when the entire discharge box 9 is raised using the grip sections 97, as best shown in FIG. 11, a configuration is produced in which the main body 90 and lid 91 are suspended by the handle 92. Consequently, even if the aperture area at the aperture 30 of the casing 3 is set to be smaller than the area of the bottom wall 93E of the main body 90, insertion and removal of the discharge box 9 can be performed through the aperture 30 of the casing 3 when this is opened at the top. In this way, insertion/removal of the discharge box 9 with respect to the casing 3 can be performed easily and reliably even when arranged adjacent to another analytical apparatus at the side of the analytical apparatus 1, or even when implements necessary for performing analysis etc are arranged in front of the analytical apparatus 1. Also, since another analytical apparatus or the like can be arranged beside the analytical apparatus 1 in a condition adjacent thereto, the degree of freedom of the apparatus layout is increased, and spatial efficiency when arranging the apparatus can be improved. Also, even when reagents etc are arranged in front of the analytical apparatus 1, the discharge box 9 can be inserted/removed with respect to the casing 3 without having to specially move these.

At least one or other of the lid 91 and handle 92 could be dispensed with in the discharge box 9. Also, even when a lid 91 or handle 92 is employed, it is not necessarily essential that the lid 91 or handle 92 should be permanently fitted to the main body 90. For example, by adopting a construction in which the lid 91 or handle 92 is detachable with respect to the main body 90, the lid 91 or handle 92 not being mounted thereon when the main body 90 is accommodated in the casing 3, a method of use could be adopted wherein the lid 91 or handle 92 is arranged to be mounted on the main body 90 before or after the main body 90 is extracted from the casing 3.

Although, in the present embodiment, an example has been described of analytical apparatus employing specimens wherein a plurality of reagent pads are arranged next to each other, the present invention could also be applied to analytical apparatus employing analytical tools other than the samples referred to above. In this case, it may be envisioned that the analytical tools may be fed with the drop faces (faces to which sample is supplied) in the analytical tools directed downwards. Even in such a case, feeding can be effected with the direction of the drop faces in the analytical tools made to be uniformly downwards, by using the sliding feed mechanism 5 described above.

The invention claimed is:

1. A mechanism for selecting a direction of an analytical tool, the mechanism comprising:
   a passage along which a plate-shaped analytical tool is moved, the passage having downwardly open outlet, the analytical tool being, discharged from the outlet of the passage with a leading edge of the analytical tool directed downward and with a trailing edge of the analytical tool directed upward;
   a support providing a horizontal movement path below the outlet of the passage;
   a horizontally movable block disposed on the support below the outlet of the passage and mounted for reciprocal movement along the horizontal movement path in a first horizontal direction and a second horizontal direction opposite to the first horizontal direction, the horizontally movable block being arranged to move the analytical tool in the first horizontal direction; and
   a sensor that is utilised to determine whether the drop face of the analytical tool onto which a drop sample is dispensed will be facing in the first horizontal direction or the second horizontal direction when the analytical tool is in the erect posture on the horizontally movable block;

wherein, when the horizontally movable block is directly below an outlet of the passage, the analytical tool from the passage is discharged onto the horizontally movable block with an erect posture in which the leading edge of the analytical tool engages the horizontally movable block while the trailing edge of the analytical tool engages the outlet of the passage, the horizontally movable block with the analytical tool in the erect posture thereon is moved in the first horizontal direction or moved in the second horizontal direction and then in the first horizontal direction in accordance with the determination result obtained b the sensor so as to cause the analytical tool to he placed in a horizontal condition on the horizontally movable block.

2. The mechanism according to claim 1, further comprising a groove provided on the horizontally movable block for positioning the leading edge of the analytical tool when the analytical tool is in the erect posture.

3. The mechanism according to claim 2, wherein the cross section of the groove is V-shaped.

4. The mechanism according to claim 1, wherein the horizontally movable block comprises an erect face for preventing movement of the analytical tool in the second horizontal direction on the horizontally movable block when the horizontally movable block is moved in the first horizontal direction.

5. The mechanism according to claim 1, wherein a width of the analytical tool defined as a distance between the leading edge and the trailing edge is greater than a spacing between the horizontally movable block and the outlet of the passage.

6. The mechanism according to claim 1, wherein the analytical tool further comprising a drop face onto which a drop of sample is dispensed is set to face upwards by moving the horizontally movable block in either the first horizontal direction or the second horizontal direction.

7. The mechanism according to claim 1, further comprising a guide including the passage, wherein the sensor is provided of the guide.

8. An analytical apparatus comprising:
an accommodating section for accommodating a plate-shaped analytical tool;
a passage for moving the analytical tool accommodated in the accommodating section downwardly from the accommodating section, the passage having a downwardly open outlet;
a drop dispensing section from which a drop of sample is dispensed onto the analytical tool;
an analyser analysing the sample dispensed onto the analytical tool;
a support providing a horizontal movement path below the outlet of the passage;
a horizontally movable block disposed on the support below the outlet of the passage and mounted for reciprocal movement along the horizontal movement path in a first horizontal direction toward the drop dispensing section and a second horizontal direction opposite hereto, the horizontally movable block being arranged for moving the analytical tool towards the drop dispensing section; and
a sensor utilised for determining whether the drop face of the analytical tool onto which a drop of sample is dispensed will be facing in the first horizontal direction or in the second horizontal direction when the analytical tool is in the erect posture on the horizontally movable block;

wherein, when the horizontally movable block is directly below the outlet of the passage, the horizontally movable block receives the analytical tool from the outlet of the passage with an erect posture in which a leading edge of the analytical tool engages the horizontally movable block while a trailing edge of the analytical tool engages the outlet of the passage, the horizontally movable block is moved in the first horizontal direction or moved in the second horizontal direction and then in the first horizontal direction in accordance with the determination result obtained by the sensor so as to cause the anal tool to be placed in a horizontal condition on the horizontally movable block.

9. The analytical apparatus according to claim 8, further comprising a groove provided on the horizontally movable block for positioning the leading edge of the analytical tool when the analytical tool is in the erect posture on the horizontally movable block.

10. The analytical apparatus according to claim 9, wherein the cross-section of the groove is V-shaped.

11. The analytical apparatus according to claim 8, wherein the horizontally movable block has an erect face for preventing movement of the analytical tool in the second horizontal direction on the horizontally movable block when the horizontally movable block is moved in the first horizontal direction.

12. The analytical apparatus according to claim 11, wherein the drop dispensing section further comprises an erect face to correct positional deviation of the analytical tool in the first and second horizontal directions in the drop dispensing section.

13. The analytical apparatus according to claim 12, wherein the erect face of the drop dispensing section and the horizontally movable block are adjacent to each other and configured to sandwich the analytical tool between the erect face of the horizontally movable block and an erect face of the drop dispensing section when the analytical tool is positioned in the drop dispensing section, 14. The analytical apparatus according to claim 8, wherein a width of the analytical tool defined as a distance between the leading edge and the trailing edge is greater than a spacing between the horizontally movable block and the outlet of the passage.

15. The analytical apparatus according to claim 8, further comprising a guide including the passage, wherein the sensor is provided on the guide.

* * * * *